United States Patent [19]

Treadgold

[11] Patent Number: 4,518,787

[45] Date of Patent: May 21, 1985

[54] SILYLATION PROCESS

[75] Inventor: Richard C. Treadgold, Cardiff, Wales

[73] Assignee: Dow Corning Limited, Barry, Wales

[21] Appl. No.: 589,797

[22] Filed: Mar. 15, 1984

[30] Foreign Application Priority Data

Mar. 3, 1983 [GB] United Kingdom ............... 8308823

[51] Int. Cl.$^3$ ............................ C07F 7/08; C07F 7/18
[52] U.S. Cl. .................................... 556/442; 556/470; 556/471; 260/239.1; 260/239.5; 260/397.2; 260/413; 260/398; 544/16; 544/19; 546/14; 548/110
[58] Field of Search ............... 260/239.1, 239.5, 397.2, 260/413, 398; 544/16, 19; 556/442, 470, 471; 546/14; 548/110

[56] References Cited

U.S. PATENT DOCUMENTS 3,417,120  12/1968  Boissieras et al. .............. 556/470 X
4,360,686  11/1982  Wang et al. .................... 556/470 X

OTHER PUBLICATIONS

Pierce, "Silylation of Organic Compounds", Pierce Chemical Co., Rockford, IL (1968).

*Primary Examiner*—Paul F. Shaver
*Attorney, Agent, or Firm*—Richard A. Kaba

[57] ABSTRACT

Process for silylating an organic or an organosilicon compound having at least one hydroxyl group bonded to carbon or to silicon, wherein the compound is contacted with both (i) a bis-triorganosilyl(alkylenediamine) and (ii) a triorganohalosilane.

The process can be employed for the silylation of intermediates in the production of pharmaceuticals.

4 Claims, No Drawings

SILYLATION PROCESS

This invention relates to a process for the silylation of organic and organosilicon compounds.

It is known that silyl groups may be transferred from certain organosilicon compounds to other organosilicon compounds or to organic compounds having one or more reactive hydrogen atoms in the molecule. This so-called silylation process has been employed for a number of years on a commercial scale, especially in the synthesis of pharmaceutical products. Organosilicon compounds of pharmaceutical products. Organosilicon compounds which have been employed as silylating agents in such a process include the trialkylchlorosilanes, for example trimethylchlorosilane, and certain nitrogen-containing organosilicon compounds, hexamethyldisilazane being one of those most commonly used. It is also known from British Pat. No. 760,059 to employ a mixture of a silazane and a trialkylchlorosilane as the silylating agent. However, although the presently used silylating agents perform satisfactorily there has been a continuing search for silylating agents having the advantage of improved efficiency.

British Patent Application No. 2,108,139 claims a process for silylating an organic or organosilicon compound wherein the silylating agent is a bis-triorganosilyl(alkylenediamine). Such compounds have been shown to be relatively efficient with respect to the silylation of alcoholic hydroxyl groups. However, their utility as silylating agents is restricted inasmuch as they are not generally effective in the silylation of carboxylic hydroxyl groups.

We have now surprisingly found that efficient silylation of carboxylic hydroxyl groups can be effected if a triorganohalosilane is employed in conjunction with the hereinbefore described bis-triorganosilyl(alkylenediamines). It has also been found that the presence of the triorganosilyl halosilane can, at least in some cases, further improve the efficiency of the silylation reaction with respect to alcoholic hydroxyl groups.

Accordingly the present invention provides a process for silylating an organic or an organosilicon compound which comprises contacting an organic or organosilicon compound having in the molecule one or more hydroxyl groups bonded to carbon or to silicon with both (i) a compound having the general formula $(R_3Si)NH(CH_2)_xNH(SiR_3)$ wherein each R represents an alkyl group having from 1 to 4 inclusive carbon atoms, the vinyl group or the phenyl group and x is an integer of from 2 to 6 inclusive and (ii) a compound having the general formula $R'_3SiY$, wherein each R' represents an alkyl group having from 1 to 6 inclusive carbon atoms, the vinyl group or the phenyl group and Y represents a chlorine, bromine and iodine atom.

In the general formula of the compound (i) employed according to the process of this invention R may be methyl, ethyl, propyl, butyl, vinyl or phenyl and x may be any integer from 2 to 6 inclusive. Generally, in the practice of the invention the R groups are preferably methyl. Examples of the operative compounds (i) are therefore N,N'-bis(trimethylsilyl)ethylenediamine, N,N'-bis(dimethylphenylsilyl)tetramethylenediamine, N,N'-bis(butyldimethylsilyl)pentamethylenediamine and N,N'-bis(trimethylsilyl)hexamethylenediamine. The compounds (i) may be prepared by the reaction of a triorganohalosilane e.g. $R_3SiCl$ with an alkylene diamine.

In the general formula of the trioganohalosilanes (ii) R may represent a $C_{1-6}$ alkyl group, the vinyl group or the phenyl group, but is normally preferably methyl or butyl. The substituent Y is preferably a chlorine atom. Examples of compounds (ii) are trimethylchlorosilane, phenyldimethylchlorosilane, vinyldimethyliodosilane and dimethylbutylbromosilane.

Any organic or organosilicon compound having at least one —OH group bonded directly to a carbon atom or a hydroxyl group bonded to a silicon atom may be silylated according to the process of this invention. Examples of such organic and organosilicon compounds are alcohols e.g. isopropanol, n-hexanol, octadecanol and benzyl alcohol, glycols and polyglycols e.g. ethylene glycol, hexylene glycol and hydroxy-terminated poly(alkylene oxides), phenols e.g. phenol, m-cresol, p-xylenol, pyrogallol and 2,6-di-secbutyl-phenol, acids e.g. heptanoic acid and benzoic acid and silanols and siloxanols e.g. diphenylsilanediol and 1,3-dimethyl-1,3-diphenyldisiloxanediol-1,3. The process of this invention finds particular application in the silylation of certain biologically active substances or the precursors thereof, a procedure which is carried out on the commercial scale in connection with the synthesis and modification of pharmaceutical products such as penicillins, cephalosporins and steroids.

In such commercial applications the group to be silylated is usually an —OH group, either as present in carboxy (—CO.OH) or alcoholic (≡C.OH) groups. The process of this invention may be employed for example in effecting the protective silylation of penicillin G during its conversion to 6-aminopenicillanic acid, the protective silylation of 6-aminopenicillanic acid during its conversion to 6-acylamidopenicillanic acids and the protective silyation of 7-aminocephalosporanic acid and 7-aminodesacetoxyphalosporanic acid during their conversion to 7-acylamidocephalosporanic acid and 7-acylamidodesacetoxycephalosporanic acid respectively. It may also be employed in the conversion of 6-acylamidopenicillanic acid sulphoxides to 7-acylamidodesacetoxycephalosporanic acids and the preparation of the silyl esters of azetidine 2-sulphenates.

In the performance of the process of this invention the reactants (i) and (ii) may be employed in widely varying relative proportions. As little as 0.01 mole of triorganochlorosilane (ii) per mole of bis-triorganosilyl-(alkylenediamine) may be used. For most efficient silylation, however, it is preferred to employ at least one, and more preferably two, moles of (ii) per mole of (i). The total proportion of (i) and (ii) employed will depend on the desired degree of silylation of available OH groups. Where the maximum degree of silylation is required sufficient of (i) and (ii) should be employed to provide at least one $R_3Si$— or $R'_3Si$— group per hydroxyl group.

The silylation reaction may be carried out in the presence or absence of a diluent. Diluents which may be employed include inert organic solvents, for example toluene, xylene, benzene and dimethyl formamide. Some reaction will in many cases take place spontaneously on mixing the reactants at normal temperatures. If desired, however, elevated temperatures e.g. 40° to 150° C. may be employed to expedite the reaction and/or facilitate recovery of the reaction product.

EXAMPLE 1

N,N'-bis(trimethylsilyl)ethylenediamine (0.68 g, 0.0033 mole), trimethylchlorosilane (0.36 g, 0.0033 mole), 2,6-di-secbutylphenol (2.06 g, 0.01 mole) and dry dichloromethane (5 ml) were mixed together and maintained at 30° C. for 3 minutes. Examination of the mixture by gas liquid chromatography after this time had elapsed showed that 80% by weight of the phenol reactant had been converted to 2,6-di-secbutylphenoxytrimethylsilane.

The process was repeated except that the N,N'-bis(trimethylsilyl)ethylenediamine was employed in a proportion of 0.0025 mole (0.51 g) and the trimethylchlorosilane in a proportion of 0.005 mole (0.54 g). The yield of the silylated phenol was 88.8%.

For purposes of comparison the above described reaction was repeated employing the same reaction conditions but with the diamine/chlorosilane combination replaced in turn by known silylating agents. Sufficient of the known silylating agents was employed to provide one silyl group for each hydroxyl group. The percentage conversions obtained were as follows:

| | |
|---|---|
| Hexamethyldisilazane | 4.2 |
| Hexamethyldisilazane/CH$_3$SiCl (equimolar mixture) | 7.2 |
| Trimethylsilyldiethylamine | 20.9 |
| N,N'bis(trimethylsilyl)urea | 9.0 |

EXAMPLE 2

To hexan-1-ol (5.1 g, 0.05 mole) in dichloromethane (50 ml) were added trimethylchlorosilane (1.81 g, 0.0166 mole) and N,N'-bis(trimethylsilyl)ethlenediamine (3.44 g, 0.0166 mole). The mixture was stirred under reflux for 30 minutes, filtered and the solvent removed. The residue, hexanoxytrimethylsilane, was obtained in 59% yield (5.15 g).

The process was repeated except that the diamine reactant was replaced by bis(trimethylsilyl)hexamethylene diamine (0.0166 mole). The compound hexanoxytrimethylsilane was obtained in 70% yield.

EXAMPLE 3

Heptanoic acid (6.5 g, 0.05 mole) in acetonitrile (50 ml) was reacted with bis(trimethylsilyl)ethylene diamine (3.44 g, 0.0166 mole) and trimethylchlorosilane (1.81 g, 0.0166 mole) as described in Example 2. The desired product trimethylsilylheptanoate was obtained in 20% yield.

When the process was repeated employing 0.025 mole of trimethylchlorosilane and 0.0125 mole of the bis(trimethylsilyl)ethylenediamine the yield of the product increased to 45%.

For comparison heptanoic acid (6.5 g, 0.05 mole), acetonitrile (50 ml) and bis(trimethylsilyl)ethylenediamine (6.12 g, 0.03 mole) were mixed together and the mixture refluxed for 30 minutes. When the solvent was removed and the remaining product fractionated no trimethylsilylheptanoate was found.

EXAMPLE 4

The procedure of Example 3 was repeated except that the diamine was replaced with bis(trimethylsilyl)hexamethylene diamine. The yield of product was 30% when equimolar proportions of diamine and silane were employed and 55% when the molar proportion of trimethylchlorosilane was doubled.

That which is claimed is:

1. A process for silylating an organic or an organosilicon compound which comprises contacting an organic or an organosilicon compound having in the molecule one or more hydroxyl groups bonded to carbon or to silicon with both (i) a compound having the general formula

$(R_3Si)NH(CH_2)_xNH(SiR_3)$ wherein each R represents an alkyl group having from 1 to 4 inclusive carbon atoms, the vinyl group or the phenyl group and x is an integer of from 2 to 6 inclusive and (ii) a compound having the general formula R'$_3$SiY, wherein each R' represents an alkyl group having from 1 to 6 inclusive carbon atoms, the vinyl group or the phenyl group and Y represents a chlorine, bromine or iodine atom.

2. A process as claimed in claim 1 wherein each R is methyl.

3. A process as claimed in claim 1 wherein each R' is selected from methyl groups and butyl groups.

4. A process as claimed in claim 1 wherein at least one mole of (ii) is employed per mole of (i).

* * * * *